United States Patent [19]

Yanagida et al.

[11] Patent Number: 5,264,611
[45] Date of Patent: Nov. 23, 1993

[54] PROCESS FOR PREPARING TRANS-β-AROYLACRYLIC ESTER

[75] Inventors: Yoshifumi Yanagida, Kakogawa; Shingo Matsumoto, Himeji; Satomi Takahashi, Kobe, all of Japan

[73] Assignee: Kanegafuchi Kagaku Kabushiki Kaisha, Osaka, Japan

[21] Appl. No.: 816,555

[22] Filed: Jan. 6, 1992

[30] Foreign Application Priority Data

Jan. 9, 1991 [JP] Japan .................................. 3-000980

[51] Int. Cl.$^5$ .............................................. C07C 69/76
[52] U.S. Cl. ....................................... 560/51; 560/23; 560/53; 560/186; 550/414
[58] Field of Search ..................... 560/51, 23, 53, 186

[56] References Cited

FOREIGN PATENT DOCUMENTS 62-15060  4/1987  Japan .
2075836  11/1981  United Kingdom .
2107714  5/1983  United Kingdom .
2108385  5/1983  United Kingdom .

*Primary Examiner*—Paul J. Killos
*Attorney, Agent, or Firm*—Armstrong, Westerman, Hattori, McLeland & Naughton

[57] ABSTRACT

A process for preparing a trans-β-aroylacrylic ester which comprises reacting an aryl methyl ketone and an alkyl acetal of alkyl glyoxylate in the presence of an acid catalyst with heating.

This process is excellent in operability, safety and ecomony and therefore is industrially advantageous process.

3 Claims, No Drawings

PROCESS FOR PREPARING TRANS-β-AROYLACRYLIC ESTER

BACKGROUND OF THE INVENTION

The present invention relates to an industrially advantageous process for preparing a trans-β-aroylacrylic ester having the formula (III):

$$A-\overset{O}{\underset{\|}{C}}-\overset{H}{\underset{|}{C}}=\underset{\underset{H}{|}}{C}-COOR^1 \quad (III)$$

wherein $R^1$ is an alkyl group having 1 to 4 carbon atoms and A is an aryl group which may be substituted by at least one substituent selected from the group consisting of a halogen atom, hydroxyl group, nitro group, cyano group, an alkyl group having 1 to 4 carbon atoms, an alkoxyl group having 1 to 4 carbon atoms and trifluoromethyl group, which is important as an intermediate material for preparing a medicament, a perfume or the like.

Hitherto, various processes have been known as processes for synthesizing an aroylacrylic ester. For example, in case of a benzoylacrylic ester, following processes have been known.

(1) A process esterifying a benzoylacrylic acid (See Comptes Rendus Hebdomadaires des Seances de l'Academie des Sciences, Serie BCD, 232, 2326 (1951) [CA, Vol 46, 943], Japanese Unexamined Patent Publication No. 103042/1987 and Japanese Unexamined Patent Publication No. 130564/1988.)

(2) A process eliminating a substituent from a benzoylpropionic ester having a substituent at the α- or β-position.

i) A process dehydrohalogenating a benzolylpropionic ester having a halogen atom at the α-position (See Journal of American Chemical Society, 45, 233 (1923) and Bulletin de la Societe Chimique de France, 1075 (1950).)

ii) A process eliminating an alcohol from a benzoylpropionic ester having an alkoxyl group at the α-position (See Japanese Unexamined Patent Publication No. 103042/1987.)

iii) A process eliminating pyrrolidine from a benzoylpropionic ester having pyrrolidinyl group at the α-position (See Tetrahedron Letters, 29, 3997 (1988).)

iv) A process eliminating methylsulfenic acid from a benzoylpropionic ester having methylsulfinyl group at the β-position (See Journal of American Chemical Society, 98, 3305 (1976).)

v) A process eliminating phenylsulfenic acid from a benzoylpropionic ester having phenylsulfinyl group at the α-position (See Tetrahedron Letters, 24, 323 (1983).)

(3) A process according to Wittig reaction with an arylglyoxal and an alkyl glyoxylate (See Collection of Czechoslovak Chemical Communications, 37, 3950 (1972) [CA, 78, 83984].)

However, in case of the process (1) esterifying a benzoylacrylic acid, the material, a benzoylacrylic acid itself should be synthesized according to a process such as Friedel-Crafts reaction of a benzene with maleic anhydride/aluminium chloride (see Journal of American Chemical Society, 70, 3356 (1948)) or aldol condensation of an acetofenone with glyoxylic acid/acetic acid (see Japanese Examined Patent Publication No. 39020/1977), wherein complicated operations are required for treatment of effluent, and it is complicated to control the formation of byproducts during esterification. Therefore, the process (1) is not necessarily recognized to be an advantageous process.

In both cases of the process (2) eliminating a substituent and the process (3) according to Wittig reaction, expensive materials are used, reaction processes are long and yields are low. Therefore, the processes (2) and (3) are not recognized to be practically useful in the industry.

An object of the invention is to provide a novel process for preparing a trans-β-aroylacrylic ester which is excellent in operability, safety, economy and the like and is therefore practically useful in the industry, solving the above mentioned problems.

SUMMARY OF THE INVENTION

It has now been found that a trans-β-aroylacrylic ester can be very efficiently prepared by reacting an aryl methyl ketone and an acetal of glyoxylic ester in the presence of an acid with heating.

The present invention relates to a process for preparing a trans-β-aroylacrylic ester having the formula (III):

$$A-\overset{O}{\underset{\|}{C}}-\overset{H}{\underset{|}{C}}=\underset{\underset{H}{|}}{C}-COOR^1 \quad (III)$$

wherein $R^1$ is an alkyl group having 1 to 4 carbon atoms and A is an aryl group which is non-substituted or substituted by at least one substituent selected from the group consisting of a halogen atom, hydroxyl group, nitro group, cyano group, an alkyl group having 1 to 4 carbon atoms, an alkoxyl group having 1 to 4 carbon atoms and trifluoromethyl group which comprises reacting an alkyl acetal of alkyl glyoxylate having the formula (I):

$$R^1O-\underset{\underset{OR^2}{|}}{CH}-COOR^1 \quad (I)$$

wherein $R^1$ is the same as defined above and $R^2$ is hydrogen atom or the same as $R^1$ and an aryl methyl ketone having the formula (II):

$$A-\overset{O}{\underset{\|}{C}}-CH_3 \quad (II)$$

wherein A is the same as defined above, in the presence of an acid with heating.

DETAILED DESCRIPTION

In the present invention, a trans-β-aroylacrylic ester can be obtained by reacting an alkyl acetal of alkyl glyoxylate and an aryl methyl ketone in the presence of an acid catalyst with heating.

Though a material to be used, an alkyl acetal of alkyl glyoxylate, is not particularly limited, an alkyl hemiacetal of alkyl glyoxylate is preferable. An alkyl fulacetal of alkyl glyoxylate is, of course, also usable and an optional mixture of an alkyl hemiacetal of alkyl glyoxylate and an alkyl fulacetal of alkyl glyoxylate can be advantageously used. Therefore, crude mixture of alkyl acetals of alkyl glyoxylate which are prepared from glyoxylic acid and an alcohol can be used as it is without isolation.

As an aryl methyl ketone, there are, for example, acetophenone which may be substituted by one or more substituents selected from the group consisting of fluorine atom, chlorine atom, bromine atom, hydroxyl group, nitro group, cyano group, an alkyl group having 1 to 4 carbon atoms, an alkoxyl group having 1 to 4 carbon atoms and trifluoromethyl group, biphenyl methyl ketone, a substituted biphenyl methyl ketone, naphtyl methyl ketone, a substituted naphtyl methyl ketone, furyl methyl ketone, a substituted furyl methyl ketone, thienyl methyl ketone, a substituted thienyl methyl ketone, pyrrolyl methyl ketone, a substituted pyrrolyl methyl ketone, oxazolyl methyl ketone, a substituted oxazolyl methyl ketone, iso-oxazolyl methyl ketone, a substituted iso-oxazolyl methyl ketone, pyrazolyl methyl ketone, a substituted pyrazolyl methyl ketone, benzofuranyl methyl ketone, indolyl methyl ketone, benzothiazolyl methyl ketone and the like.

The amount of an aryl methyl ketone to be used is not particularly limited. It is, however, economical to use 0.5 to 2 molar equivalents, preferably equal molar equivalent per molar equivalent of an alkyl acetal of alkyl glyoxylate.

In the reaction system of an alkyl acetal of alkyl glyoxylate and an aryl methyl ketone in the presence of an acid with heating, alkyl acetals of alkyl glyoxylate which are prepared from glyoxylic acid and an alcohol can be also used as it is in the reaction system, as mentioned above. That is, the reaction can be carried out by so-called one pot reaction wherein all of glyoxylic acid, an alcohol and an aryl methyl ketone are mixed together and an acid catalyst is added thereto to carry out the reaction. As alcohols usable here, there are, for example, methanol ethanol, n-propanol iso-propanol, n-butanol, iso-butanol, sec-butanol, tert-butanol and the like.

Acid catalysts to be used are not particularly limited. As such acid catalysts, there are, for example, inorganic acids such as sulfuric acid and hydrochloric acid, organic acids such as paratoluenesulfonic acid and methanesulfonic acid, Lewis acids such as boron trifluoride and the like. The amount of these acids to be used is 0.001 to 0.5 molar equivalent, preferably 0.01 to 0.1 molar equivalent per molar equivalent of an alkyl acetal of alkyl glyoxylate.

The reaction temperature is 50° to 200° C., preferably 80° to 150° C. When the reaction temperature is not less than 80° C., the rate of the reaction becomes high and when not more than 150° C., decomposition and coloring of the products can be further inhibited.

Further, the reaction can be accelerated by removing water and/or an alcohol produced with the progress of the reaction, out of the reaction system. In order to positively carry out this acceleration of the reaction, a solvent which is capable of removing water and/or an alcohol by azeotropic distillation, is preferably used. As such solvents, for example, aromatic solvents such as benzene, toluene, xylene and ethylbenzene, halogenated hydrocarbons such as 1,2-dichloroethane, trichloroethane and tetrachloroethane and the like can be advantageously used.

The refluxing state at a prescribed temperature can be maintained by keeping the reaction system constantly at a pressure within a range from a slightly high pressure to a slightly low pressure. However, it is generally preferable from the viewpoint of operability that stable refluxing state is achieved at atmospheric pressure by selecting a solvent having specific azeotropic temperature.

The reaction generally completes for 4 to 40 hours. The reaction time, however, varies depending on the reaction temperature. Since excessive reaction results in an increase of byproducts due to decomposition and a lowering of the purity of the products, it is desirable that an end point of the reaction is suitably determined grasping the quantitative change of remaining aryl methyl ketone.

After the reaction, the desired trans-$\beta$-aroylacrylic ester (III) can be obtained by usual extracting and distilling methods.

According to the present invention, a trans-$\beta$-aroylacrylic ester can be safely prepared in a high yield with inexpresive materials in a short reaction process, without complicated operations such as a treatment of effluent and a control of the formation of byproducts.

The process of the present invention is more specifically described and explained by means of the following Examples in which all percents are by weight unless otherwise noted.

It is to be understood that the present invention is not limited to the Examples, and various changes and modifications may be made in the invention without departing from the spirit and scope thereof.

The determinations of trans-$\beta$-aroylacrylic esters and aryl methyl ketones were carried out by high pressure liquid chromatography (HPLC) with following particulars.

Column: COSMOSIL 5C$_{18}$-AR made by Nacalai tesque 4.6 mm i.d.×250 mm
Mobile phase: 50% acetonitrile in 0.1M phosphate buffer (pH 2.5)
Flow rate: 1.0 ml/min.
Column temperature: 30° C.
Detection: UV 210 nm

EXAMPLE 1

A mixture of 2.0 g of methyl hemiacetal of methyl glyoxylate, 1.99 g of acetophenone, 0.12 g of monohydrate of para-toluenesulfonic acid and 20 ml of toluene was introduced into a 100 ml three neck flask provided with a fractional distillation apparatus, and was stirred to carry out the reaction at 110° C. for 5 hours with distilling away mixed solvent of water, methanol and toluene which was produced during the reaction till the total volume of the reaction mixture became approximately half. After cooling the reaction mixture by allowing to stand, the reaction mixture was distributed between toluene-water phases. The toluene phase was washed with saturated aqueous solution of sodium hydrogencarbonate and successively with water, and dried over anhydrous sodium sulfate. The solvent was distilled away under reduced pressure to give 3.25 g of yellow oil containing 2.54 g of methyl trans-$\beta$-benzoylacrylate.

The results of the determination by $^1$H-NMR are shown as follows.

$^1$H-NMR (solvent: CDCl$_3$) $\delta$ (ppm): 8.15–7.32 (phenyl, 5H, m), 7.95 (olefin, H, d), 6.88 (olefin, H, d), 3.85 (methyl in ester moiety R$^1$, 3H, s)

EXAMPLE 2

A mixture of 3.0 g of ethyl hemiacetal of ethyl glyoxylate, 2.43 g of acetophenone, 0.15 g of monohydrate of para-toluene sulfonic acid and 30 ml of toluene was stirred to carry out the reaction at 110° C. for 5 hours with distilling away mixed solvent of water, ethanol and toluene which was produced during the reaction, in the same way as in Example 1. Then the treatment of Example 1 was repeated to give 4.01 g of yellow oil containing 3.26 g of ethyl trans-β-benzoylacrylate.

The results of the determination by $^1$H-NMR are shown as follows.

$^1$H-NMR (solvent: CDCl$_3$) δ (ppm): 8.18–7.30 (phenyl, 5H, m), 7.95 (olefin, H, d), 6.92 (olefin, H, d), 4.33 (methylene in ester moiety R$^1$, 2H, q), 1.35 (methyl in ester moiety R$^1$, 3H, t)

EXAMPLE 3

A mixture of 3.0 g of ethyl hemiacetal of ethyl glyoxylate, 2.43 g of acetophenone, 0.04 g of sulfuric acid and 30 ml of toluene was stirred to carry out the reaction at 110° C. for 5 hours with distilling away mixed solvent of water, ethanol and toluene which was produced during the reaction in the same way as in Example 1. Then the treatment of Example 1 was repeated to give 3.88 g of yellow oil containing 3.18 g of ethyl trans-β-benzoylacrylate.

EXAMPLE 4

A mixture of 2.0 g of ethyl fulacetal of ethyl glyoxylate, 1.37 g of acetophenone, 0.02 g of sulfuric acid and 20 ml of toluene was stirred to carry out the reaction at 110° C. for 12 hours with distilling away mixed solvent of ethanol and toluene which was produced during the reaction, in the same way as in Example 1. Then, the treatment of Example 1 was repeated to give 2.20 g of yellow oil containing 1.76 g of ethyl trans-β-benzoylacrylate.

EXAMPLE 5

A mixture of 2.0 g of monohydrate of glyoxylic acid, 0.17 g of monohydrate of paratoluene sulfonic acid, 10 ml of ethanol and 20 ml of toluene was introduced into a 100 ml three neck flask provided with a fractional distillation apparatus, and was heated under reflux for 2.5 hours.

The above obtained product was analyzed by HPLC. As a result of the analysis, the ratio of formed ethyl hemiacetal of ethyl glyoxylate and ethyl fulacetal of ethyl glyoxylate was found to be 93:7. After ethanol was distilled away from the reaction solution with a fractional distillation apparatus, 2.61 g of acetophenone and 10 ml of toluene were added to the mixture. The mixture was stirred to carry out the reaction at 110° C. for 10 hours with distilling away mixed solvent of water, ethanol and toluene which was produced during the reaction. Then, the treatment of Example 1 was repeated to give 3.91 g of yellow oil containing 3.23 g of ethyl trans-β-benzoylacrylate.

EXAMPLE 6

Water was distilled away from 100 g of 50% aqueous solution of glyoxylic acid to be concentrated to give 75% solution under reduced pressure in an evaporator. A mixed solvent of 1.36 g of sulfuric acid, 200 ml of ethanol and 300 ml of toluene was added thereto and the mixture was heated under reflux for 3 hours. The above obtained product was analyzed by HPLC. As a result of the analysis, the ratio of formed ethyl hemiacetal of ethyl glyoxylate and ethyl fulacetal of ethyl glyoxylate was found to be 95:5. After ethanol was distilled away from the reaction solution with a fractional distillation apparatus, 81.1 g of acetophenone and 300 ml of toluene were added to the mixture. The mixture was stirred to carry out the reaction at 110° C. for 17 hours with distilling away mixed solvent of water, ethanol and toluene which was produced during the reaction. Then, the treatment of Example 1 was repeated to give 123.0 g of yellow oil containing 100.7 g of ethyl trans-β-benzoylacrylate. Subsequently, the oil was vacuum distilled with aeration of slight amount of nitrogen at a wall temperature of 130°–140° C. (bp. 117°–120° C./1 mmHg) to give 94.3 g of pure ethyl trans-β-benzoylacrylate.

EXAMPLE 7

Water was distilled away from 100 g of 50% aqueous solution of glyoxylic acid to be concentrated to give 75% solution under reduced pressure in an evaporator. A mixed solvent of 1.36 g of sulfuric acid, 200 ml of ethanol, 81.1 g of acetophenone and 300 ml of toluene was added thereto and the mixture was heated under reflux for 3 hours. After ethanol was distilled away from the reaction solution with a fractional distillation apparatus, 300 ml of toluene was added to the mixture. The mixture was stirred to carry out the reaction at 110° C. for 15 hours with distilling away mixed solvent of water, ethanol and toluene which was produced during the reaction. Then, the treatment of Example 1 was repeated to give 126.2 g of yellow oil containing 104.6 g of ethyl trans-β-benzoylacrylate.

EXAMPLE 8

Water was distilled away from 20 g of 50% aqueous solution of glyoxylic acid to be concentrated to give 75% solution under reduced pressure in an evaporator. A mixed solvent of 0.27 g of sulfuric acid, 40 ml of ethanol, 16.3 g of acetophenone and 30 ml of benzene was added thereto and the mixture was heated under reflux for 3 hours. After ethanol was distilled away from the reaction solution with a fractional distillation apparatus, 30 ml of benzene was added to the mixture. The mixture was stirred to carry out the reaction at 80° C. for 20 hours with distilling away mixed solvent of water, ethanol and benzene which was produced during the reaction. Then, the treatment of Example 1 was repeated to give 25.3 g of yellow oil containing 20.4 g of ethyl trans-β-benzoylacrylate.

EXAMPLE 9

Water was distilled away from 20 g of 50% aqueous solution of glyoxylic acid to be concentrated to give 75% solution under reduced pressure in an evaporator. A mixed solvent of 0.27 g of sulfuric acid, 40 ml of ethanol and 30 ml of xylene was added thereto and the mixture was heated under reflux for 3 hours. After addition of 16.3 g of acetophenone, ethanol was distilled away from the reaction solution under gradually reduced pressure in an aspirator. Thereto was added 30 ml of xylene and the mixture was stirred to carry out the reaction at 120° C. for 8 hours with distilling away mixed solvent of water, ethanol and xylene which was produced during the reaction, with a fractional distillation apparatus under reduced pressure at 150 mmHg. Then, the treatment of Example 1 was repeated to give 24.8 g of yellow oil containing 21.3 g of ethyl trans-β-benzoylacrylate.

EXAMPLE 10

Water was distilled away from 20 g of 50% aqueous solution of glyoxylic acid to be concentrated to give 75% solution under reduced pressure in an evaporator. A mixed solvent of 0.27 g of sulfuric acid, 40 ml of ethanol and 30 ml of toluene was added thereto and the mixture was heated under reflux for 3 hours. After ethanol was distilled away from the reaction solution with a fractional distillation apparatus, 22.3 g of paranitroacetophenone and 30 ml of toluene were added to the mixture. The mixture was stirred to carry out the reaction at 110° C. for 15 hours with distilling away mixed solvent of water, ethanol and toluene which was produced during the reaction. Then, after the treatment of Example 1 was repeated, the recrystallization was carried out with ethyl acetate to give 20.9 g of ethyl trans-β-(p-nitrobenzoyl)acrylate. The melting point of the obtained compound was 69.0°–70.0° C.

The results of the determination by $^1$H-NMR are shown as follows.

$^1$H-NMR (solvent: CDCl$_3$) δ (ppm): 8.60–8.04 (phenyl, 4H, m), 7.90 (olefin, H, d), 6.90 (olefin, H, d), 4.34 (methylene of ester moiety R$^1$, 2H, q), 1.38 (methyl of ester moiety R$^1$, 3H, t)

EXAMPLE 11

Water was distilled away from 20 g of 50% aqueous solution of glyoxylic acid to be concentrated to give 75% solution under reduced pressure in an evaporator. A mixed solvent of 0.27 g of sulfuric acid, 40 ml of ethanol and 30 ml of toluene was added thereto and the mixture was heated under reflux for 3 hours. After ethanol was distilled away from the reaction solution with a fractional distillation apparatus, 20.9 g of parachloroacetophenone and 30 ml of toluene were added to the mixture. The mixture was stirred to carry out the reaction at 110° C. for 15 hours with distilling away mixed solvent of water, ethanol and toluene which was produced during the reaction. After the treatment of Example 1 was repeated, the recrystallization was carried out with ethyl acetate to give 20.5 g of ethyl trans-β-(p-chlorobenzoyl)acrylate. The melting point of the obtained compound was 61.0°–62.0° C.

The results of the determination by $^1$H-NMR are shown as follows.

$^1$H-NMR (solvent: CDCl$_3$) δ (ppm): 8.34–7.33 (phenyl, 4H, m), 7.90 (olefin, H, d), 6.90 (olefin, H, d), 4.33 (methylene in ester moiety R$^1$, 2H, q), 1.44 (methyl in ester moiety R$^1$, 3H, t)

EXAMPLE 12

Water was distilled away from 20 g of 50% aqueous solution of glyoxylic acid to be concentrated to give 75% solution under reduced pressure in an evaporator. A mixed solvent of 0.27 g of sulfuric acid, 40 ml of ethanol and 30 ml of toluene was added thereto and the mixture was heated under reflux for 3 hours. After ethanol was distilled away from the reaction solution with a fractional distillation apparatus, 20.3 g of paramethoxyacetophenone and 30 ml of toluene were added to the mixture. The mixture was stirred to carry out the reaction at 110° C. for 15 hours with distilling away mixed solvent of water, ethanol and toluene which was produced during the reaction. Then, the treatment of Example 1 was repeated to give 30.4 g of yellow oil containing 23.1 g of ethyl trans-β-(p-methoxybenzoyl)acrylate.

The results of the determination by $^1$H-NMR are shown as follows.

$^1$H-NMR (solvent: CDCl$_3$) δ (ppm): 8.13–6.80 (phenyl, 4H, m), 7.89 (olefin, H, d), 6.82 (olefin, H, d), 4.27 (methylene in ester moiety R$^1$, 2H, q), 3.86 (methoxy, 3H, c), 1.33 (methyl in ester moiety R$^1$, 3H, t)

In addition to the ingredients used in the Examples, other ingredients can be used in the Examples as set forth in the specification to obtain substantially the same results.

What we claim is:

1. A process for preparing a trans-β-aroylacrylic ester of the formula

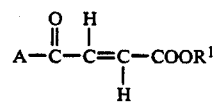

wherein R$^1$ is an alkyl group having 1 to 4 carbon atoms and A is an aryl group which is unsubstituted or substituted by at least one substituent selected from the group consisting of a halogen, hydroxyl, nitro, cyano, trifluoromethyl and an alkyl group having 1 to 4 carbon atoms, which comprises reacting at least one acetal of an alkyl glyoxylate of the formula

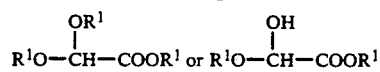

with an aryl methyl ketone of the formula

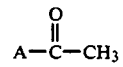

at a temperature of 80° to 120° C. in the presence of an acid and in a solvent which forms an azeotropic mixture with water and R$^1$OH, and removing water and R$^1$OH formed during the reaction by azeotropic distillation with the solvent.

2. A process according to claim 1, wherein the at least one acetal of an alkyl glyoxylate is prepared by reacting glyoxylic acid with an alcohol of the formula R$^1$-OH in the presence of an acid and in a solvent which forms an azeotropic mixture with water and R$^1$OH, and then separating water formed during the reaction and unreacted R$^1$OH by distillation prior to addition of the aryl methyl ketone.

3. The process according to claim 1 or 2, wherein the acid is an acid of the formula R$^3$-SO$_3$H, wherein R$^3$ is a hydroxyl group, an alkyl group having 1 to 4 carbon atoms or an unsubstituted or substituted phenyl group.

* * * * *